(12) United States Patent
Fleming et al.

(10) Patent No.: US 6,298,727 B1
(45) Date of Patent: Oct. 9, 2001

(54) APPARATUS FOR ACOUSTIC INSPECTION OF A WORKPIECE IN ARBITRARY SCANNING ORIENTATIONS

(75) Inventors: Marvin F. Fleming, Los Altos; Peter M. Patterson, Livermore, both of CA (US)

(73) Assignee: Sierra Matrix, Inc., Fremont, CA (US)

( * ) Notice: Subject to any disclaimer, the term of this patent is extended or adjusted under 35 U.S.C. 154(b) by 0 days.

(21) Appl. No.: 09/692,827

(22) Filed: Oct. 18, 2000

Related U.S. Application Data

(60) Provisional application No. 60/160,122, filed on Oct. 18, 1999.

(51) Int. Cl.[7] ........................................ G01N 29/14
(52) U.S. Cl. ........................ 73/644; 73/642; 73/661
(58) Field of Search ........................ 73/644, 661, 642, 73/620, 629

(56) References Cited

U.S. PATENT DOCUMENTS

| | | | |
|---|---|---|---|
| 4,058,000 | * 11/1977 | Ries et al. | 73/644 |
| 5,469,744 | * 11/1995 | Patton et al. | 73/644 |
| 5,473,943 | * 12/1995 | Barry | 73/644 |
| 5,631,425 | * 5/1997 | Wang et al. | 73/606 |
| 5,948,985 | * 9/1999 | Brautigan et al. | 73/622 |

* cited by examiner

Primary Examiner—Hezron Williams
Assistant Examiner—Jacques Saint-Surin
(74) Attorney, Agent, or Firm—Allston L. Jones

(57) ABSTRACT

An acoustic inspection device having a transducer housing opening to a face of the device to be disposed opposite a workpiece to be inspected. That face of the device having selectively located multi-piece flexible material of a selected length extending outward therefrom disposed to interface with the surface of the workpiece. A first portion of the flexible material is supplied to create, and surround, a region close to the opening of the transducer housing with a plurality of couplant supply ports around the transducer opening to form a chamber into which couplant is continuously supplied to couple the transducer to the surface of the workpiece. A second portion of the flexible material being spaced outward from, and surrounding, the first of the flexible material to create another chamber having vacuum ports in the face of the device opening into that chamber to recover couplant that leaks through the first portion of the flexible material from the couplant chamber. The flexible material is also provided to automatically locally adjust to the uneven surface of the workpiece while maintaining contact to that surface. To permit the use of the device in any orientation from horizontal, through various angles, to fully inverted, the couplant is provided independent of gravity feed with the vacuum being sufficient to recover the leaked couplant in any orientation of the device.

1 Claim, 2 Drawing Sheets

APPARATUS FOR ACOUSTIC INSPECTION OF A WORKPIECE IN ARBITRARY SCANNING ORIENTATIONS

CROSS REFERENCE

This patent application claims priority from U.S. Provisional Patent Application entitled "APPARATUS FOR ACOUSTIC INSPECTION OF A WORKPIECE IN ARBITRARY SCANNING ORIENTATIONS" having Ser. No. 60/160,122 and filed on Oct. 18, 1999.

FIELD OF THE INVENTION

The present invention relates to an apparatus and method for acoustically inspecting a workpiece in arbitrary orientation.

BACKGROUND OF THE INVENTION

Nondestructive Inspection (NDI) determines the quality of a workpiece without causing damage to the workpiece. One NDI technique uses acoustic waves to inspect a workpiece. This technique directs an incident acoustic wave at a workpiece, senses a reflection from the workpiece and analyzes the reflection to determine the quality of the workpiece. Acoustic inspection is helpful, for example, to determine the integrity of airplane components including the wing, fuselage and empennage by detecting disbonded lap splices, corroded rivet joints and similar structural defects.

A typical apparatus for acoustically inspecting a workpiece includes a pulse generator electrically connected to a transducer assembly which generates a focused acoustic wave (practical ultrasonic transducers have an inherent focus and the selection of a useful focus is application dependant). The acoustic wave travels through a transmission medium and onto the workpiece. Acoustic reflections from the workpiece radiate back to the transducer and causes the transducer to generate a corresponding electrical signal. A processor then analyzes the electrical signal to determine the quality of the workpiece.

Ultrasonic NDI, in particular can improve the inspection spatial resolution and the signal to noise by using a focused acoustic beam and a scanner to move the transducer assembly in a raster scan over the workpiece. This type of NDI requires good and reliable acoustic coupling and is most effective when applied in an immersion mode.

A known inspection apparatus as described by Patton in the U.S. Pat. No. 5,469,744 uses an acoustic apparatus called a Contact Adaptive Bubbler (CAB) consisting of a tubular member containing an ultrasonic transducer and a couplant chamber (first chamber) and a couplant reservoir (second chamber) between the transducer and the workpiece. Couplant is continuously supplied to replenish couplant leaks. A vacuum chamber (opening) recovers couplant that leaks from the couplant reservoir (second chamber).

However, in practice, it was found that the prior art inspection device operates reliably on horizontal and slightly angled workpiece surfaces, but not on rough surfaces, and in vertical and underside orientations (inverted) with respect to workpiece surfaces. Further, the couplant and vacuum lines connected to prior art devices easily disturbs the horizontal and slightly angled orientations of those device with respect to the workpiece, thus minimizing the reliability of the prior art devices even in those orientations. Additionally, the prior art devices cannot reliably be used on rough surfaces, or vertical or under side surfaces as a result of shortcomings of the interface of those devices to the surface of interest. The acoustic inspection device of the present invention overcome the problems experienced by the prior art thus permitting use on rough surfaces and in any orientation from horizontal to inverted.

SUMMARY OF THE INVENTION

An object of the present invention is to provide an acoustic inspection device that: (1) interfaces reliably with uneven or rough workpiece surfaces; (2) interfaces reliably with all workpiece surface orientations from horizontal on top of the workpiece to inverted on the underside surfaces of the workpiece; and (3) provides a superior and reliable acoustic coupling with the workpiece independent of the orientation and condition of the workpiece surface being inspected. Accordingly, the acoustic inspection device of the present invention is compatible with surfaces that are rough or oriented at any angle including inverted on the under-side of a workpiece.

Another, object of the present invention is to provide an acoustic inspection device with a smaller diameter, flexible vacuum and couplant supply lines, and positions for the ports on the acoustic inspection device of the present invention that allow for more accurate alignment to the orientation of the workpiece, regardless of that orientation.

Yet another object of the present invention is the provision of a small footprint of the acoustic inspection device of the present invention.

The acoustic inspection device of the present invention is designed for use on a broad range of workpiece surfaces including those that have unevenness that disturb the desired orientation of the prior art devices as they pass over the rough areas. Additionally, it has been observed with the prior art devices that the surface unevenness can spoil the integrity between the couplant and the workpiece. The objective of the present invention is to greatly improve the capability for scanning uneven surfaces by using improved couplant distribution and vacuum recovery in the their respective chambers.

Each of these objects result from the combination of the various features of the present invention.

DESCRIPTION OF THE PRESENT INVENTION

The present invention provides an acoustic inspection device and inspection method for acoustically inspecting a workpiece which is described in relation to the included figures. As will be seen from the following discussion, the acoustic inspection device of the present invention can be called a contact, dripless bubbler (CDB).

Figure 1:
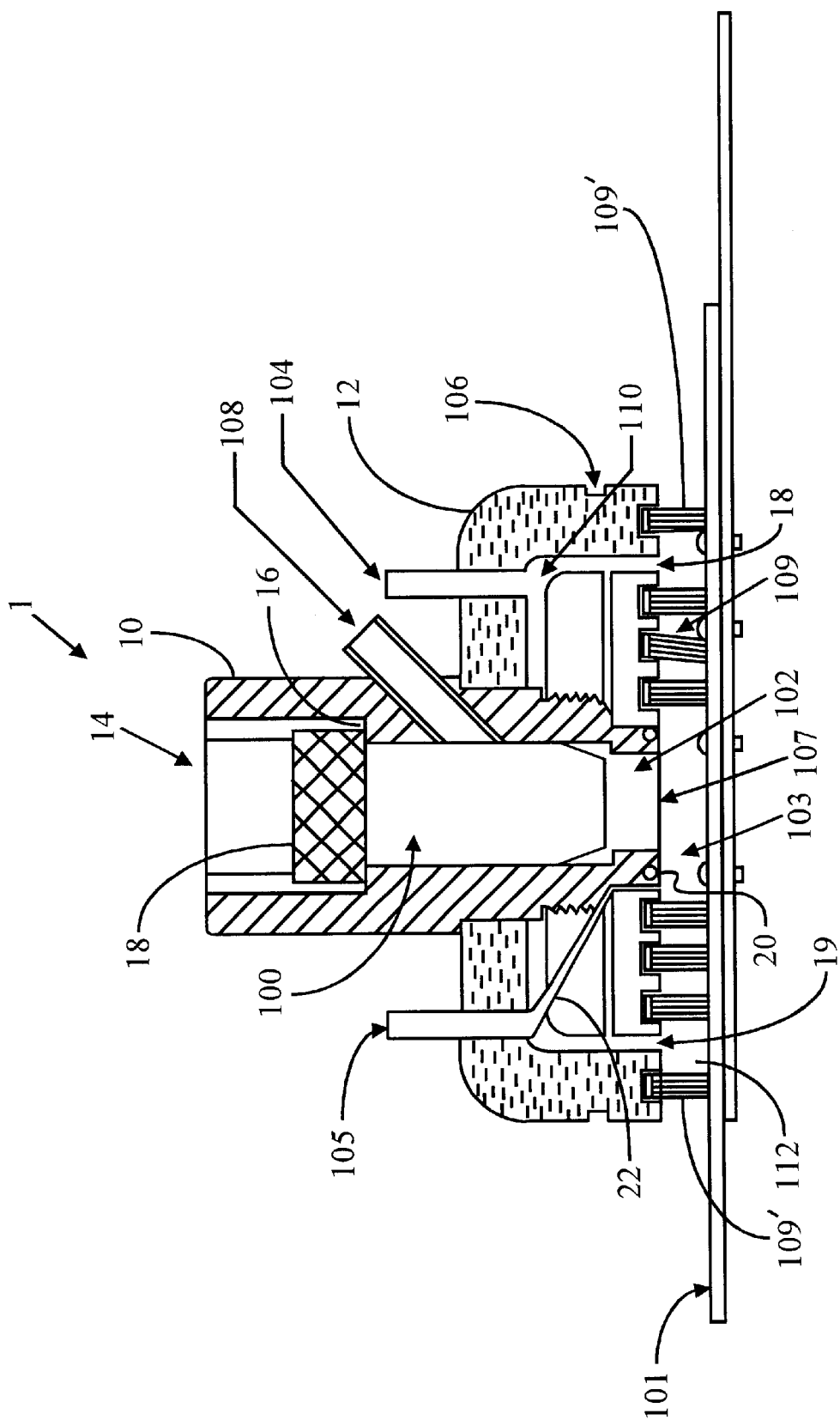
FIG. 1 is a vertical cross-section of the acoustic inspection device of the present invention.

FIG. 1 shows a vertical cross-section of acoustic inspection device 1 of the present invention that has a central body portion 10 that is surrounded in the lower extent by lower body portion 12. Central body portion 10 includes a central passage 14 therethrough that is sized and shaped to receive an immersion transducer 100.

The upper, or proximate, end of central body portion 10 provides a port into central passage 14 for insertion of immersion transducer 100, and the lowest, or distal, end of central body portion 14 includes a membrane 107 (e.g., latex less than 0.01 inches thick) to seal the distal end of central passage 14 to retain couplant in central passage 14 as further described below. Also shown in FIG. 1, near the proximate end of central body portion and internal to central passage 14 is a shoulder 16 to capture support ring 18 around immersion transducer 100 to prevent transducer 100 from bottoming out against membrane 107 when transducer 100 is in place. Further, extending through central body portion 10 and into the side of central passage 14 is a vent tube 108 with a one way exhaust ball valve therein.

Prior to insertion of transducer 100 into central passage 14, a couplant fluid (e.g., water) is added to the lower extent of central passage 14 with that fluid being retained in central passage 14 by membrane 107. Then as transducer 100 is inserted into central passage 14, air and the excess of the couplant is expelled through vent tube 108 and an internal exit only ball valve (not shown) into a small diameter (e.g., 0.1 inch diameter) drain tube (not shown) to direct the excess couplant away from acoustic inspection device 1. Once support ring 18 contacts shoulder 16 the distal end of transducer 100 is spaced apart from membrane 107 with couplant in contact with both the distal end of transducer 100 and membrane 107 in a first cavity, or chamber, 102 thus capturing the couplant therewithin. Once transducer 100 is in place and the excess couplant bleed out from first chamber 102, the drain tube attached to vent tube 108 can be removed since it is not needed during scanning of the workpiece since the couplant in first chamber 102 cannot escape.

Central body portion 1 is shown threaded into the center of lower body portion 12 with the distal end of central body portion 10 supported in a spaced apart relationship from the facing surface of workpiece 101 when acoustic inspection device 1 is in use. Defined within lower body portion 12 is vacuum path 110 that opens through the distal face of lower body portion 12 with a plurality of vacuum ports 19 spaced outward from the distal end of central body portion 10 near the outer edge of lower body portion 12. Lower body portion 12 also defines a vacuum outlet 104 therethrough that opens away from workpiece 101 and is in communication with vacuum path 110. Vacuum outlet 104, when acoustic inspection device 1 is in use, is coupled via a flexible hose (e.g., polyurethane hose with 0.25 inch outer diameter) (not shown) to a vacuum pump (not shown) that is located away from acoustic inspection device 1. While only one vacuum outlet 104 is shown in FIG. 1, additional vacuum ports can be provided as necessary to allow for the use of multiple small diameter flexible hoses which are each, and are collectively, more flexible than a single larger diameter vacuum hose. It has been observed that the use of multiple smaller diameter flexible hoses as opposed to a single larger diameter hose greatly improves the ability of acoustic inspection device 1 to remain in contact with workpiece 101 during scanning.

Lower body portion 102 further defines therethrough at least one couplant supply path 22 that opens through the distal face of lower body portion 12 in a port 20 that is located in close proximity to the distal end of central body portion 10. Also defined within lower body portion 12, in direct communication with couplant supply path 22, is couplant inlet 105 that is connected to a couplant supply source (not shown) through a flexible hose (not shown) (of a similar material and size as the vacuum hose discussed above) with the couplant source located away from acoustic inspection device 1. While only one couplant inlet 105 is shown in FIG. 1, additional couplant inlets can be provided as necessary to allow for the use of multiple small diameter flexible hoses which distribute an disturbance forces more uniformly as the orientation of the surface of workpiece 101 varies with regard to device 1 than a single larger diameter flexible hose. Port 20 is, or ports 20 are, located in close proximity to the distal end of central body portion 10 to provide couplant beneath membrane 107 into a second chamber 103 between membrane 107 and workpiece 101. As for the vacuum hoses, multiple smaller diameter flexible couplant supply hoses as opposed to a single larger diameter hose further improves the ability of acoustic inspection device 1 to remain in contact with workpiece 101 during scanning for the same reason described above with regard to the couplant supply hoses.

Additionally, lower body portion includes one or more sets of a closely packed flexible material 109 (e.g., 0.006 inch diameter, 0.25 inch long polypropylene bristles) captured within, and extending away from the distal face of lower body portion 12, that encircle the distal end of central body portion 10 between couplant supply ports 20 and vacuum ports 19. At least one additional set of closely packed flexible material 109' (similar to flexible material 109) is captured within, and extending away from the distal face of lower body portion 12, encircling the distal end of central body portion 10 outward beyond vacuum ports 19. The free ends of each set of flexible material 109 and 109' extends substantially the same distance from the distal face of lower body portion 12.

The third chamber of the present invention, vacuum chamber 112, is formed between the outer most row of flexible material 109, flexible material row 109' and workpiece 101 with vacuum chamber 112 in direct communication with vacuum ports 19.

In operation, the present invention provides and maintains reliable ultrasonic coupling between the distal face of transducer 100 and workpiece 101 through both the first and second chambers 102 and 103. First chamber 102 is always filled with couplant as described above. Second chamber 103 is maintained full of couplant by continuously resupplying lost couplant from ports 20 to assure that second chamber 103 remains full of couplant independent of the orientation of the workpiece and unevenness on the workpiece surface. Flexible material, such as brushes, are used to form second chamber 103 and to space lower body portion 12, and central body portion 10 that houses transducer 100 from workpiece 101. As the rows of flexible material 109 are somewhat porous and bend to follow any uneven surfaces on workpiece 101, couplant leaks through flexible material 109. The couplant that leaks through flexible material 109 is thus resupplied from couplant ports 20 in order to maintain second chamber 103 full continuously.

The couplant that leaks through the rows of flexible material 109 eventually reaches third chamber 112, the vacuum chamber, where the vacuum provided by vacuum ports 19 removes substantially all of the leaked couplant, which is drawn off through ports 19, vacuum path 110 and out vacuum outlet 104 and the flexible hose before the leaked couplant passes through the additional row of flexible material 109'. This vacuum configuration assures a uniform vacuum distribution for removal of couplant that leaks from second chamber 103 and further enhancing the reliability of maintaining couplant in second cavity 102 independent of the orientation of the workpiece relative to the acoustic inspection device and the roughness of the surface of the workpiece.

In operation, transducer 100 is activated to generate an acoustic wave that travels through the couplant fluid disposed in first and second chambers 102 and 103 striking the portion of workpiece 101 opposite the distal end of transducer 100. An acoustic wave is then reflected from workpiece 101 under the influence of the condition of workpiece 101. The reflected acoustic wave is then transmitted through the couplant within chambers 103 and 102, respectively, to transducer 100 which generates a corresponding electrical signal that is sent to processor equipment (not shown) that is connected to transducer 100 for evaluation. Thus it can be seen that the use of flexible material 109 and 109' of the present invention assures coupling on irregular surfaces while retaining the couplant on the surface of workpiece 101.

The multiple couplant output ports 20 and vacuum intake ports 19 assure uniform coupling of the acoustic beam into workpiece 101, for couplant removal in any orientation of the workpiece and consequently improves the operational reliability for all orientations of the acoustic inspection device 1 of the present invention. The use of multiple couplant and vacuum ports results in (a) increased following accuracy for the acoustic inspection device 1 relative to the surface orientation of the workpiece and (b) a smaller footprint for acoustic inspection device 1 on the workpiece.

Also shown in FIG. 1 are scanner attachment points 106 on opposite sides of lower body portion 12 of acoustic inspection device 1. Acoustic inspection device 1 may be attached to a scanner to accurately and repeatedly position device 1 to provide the processor with position information so that an acoustic map can be made of workpiece 101 of the regions explored.

Given all of these improvements over the prior art, the footprint, or diameter, of lower body portion 12 can also be smaller than that of the prior art devices. Acoustic inspection device 1 of the present invention can have a diameter on the order of 2 inches, while prior art devices are much larger with only a few having a diameter no smaller than 3.125 inches. Thus the smallest footprint for the prior art devices is 7.66 inches$^2$ versus 3.14 inches$^2$ for the present invention; the size of the prior art device footprint is at least 2.4 times larger than the footprint of the device of the present invention.

Figure 2:
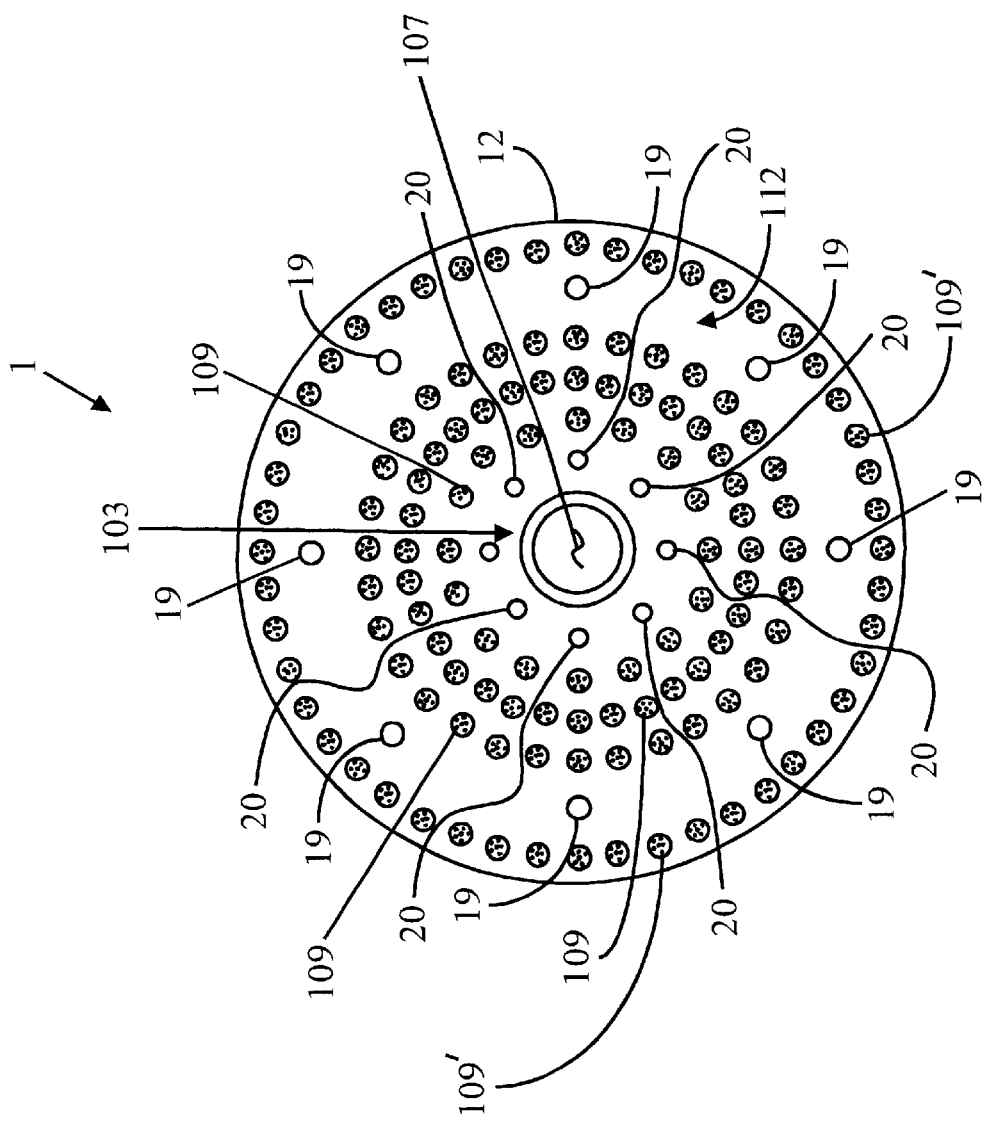
FIG. 2 is a bottom view of a non-cross-sectioned acoustic inspection device of the present invention.

FIG. 2 is a bottom view of acoustic inspection device 1 showing the details of various of the features of the present invention in a circular configuration. While in this view a circular configuration is shown, the present invention is not limited to that configuration and could be implemented in any number of configurations desired by the user. Starting in the center, there is membrane 107 surrounded by eight couplant ports 20. Extending further outward from couplant ports 20 are three concentric circular arrangements of flexible material 109. Second chamber 103 is shown here as the area enclosed within the inner most circle of flexible material 109.

Extending further outward from the center and the outer most circle of flexible material 109 are eight vacuum ports 19 with a circle of flexible material 109' yet further outward from membrane 107 beyond the circle of vacuum ports 19. Third chamber 112 is shown here as the area enclosed between the outer most circle of flexible material 109 and the circle of flexible material 109' with vacuum ports 19 opening into chamber 112.

This arrangement of individual elements of flexible material 109 is for illustrative purposes and the individual elements of flexible material 109 could be closer or further apart in each circle, the circles could be closer together, the individual elements in adjacent circles could be staggered to be opposite spaces between the individual elements of flexible material 109 in adjacent circles, and there could be a different number of circles, more or less, of flexible material 109 than shown in FIG. 2. Accordingly, the number and size of couplant ports 20 is partially determined by the viscosity and leak rate of the couplant through the selected configuration of flexible material 109, and the desired flexibility of the couplant supply hose(s) attached to inlet(s) 105. Similarly, the configuration and number of circles of flexible material 109' is dependent on several factors including the couplant viscosity and leak rate through flexible material 109, the strength of the vacuum provided by each of vacuum ports 19, and the leak rate through flexible material 109'. The number and size of vacuum ports 19 is influenced by the same factors, as well as the desired flexibility of the vacuum hose(s) connected to vacuum outlet(s) 104. Thus the numbers, size and location of the various components is a matter of design choice given the flexible material used, and the need to provide, and to maximize the recovery of, the couplant independent of gravity assist. Smaller diameter ports 19 and 20 are used as the number of ports is increased while maintaining the same quality level of ultrasonic coupling. The use of the smaller diameter, or a reduced number of, ports further allows for the reduction in the footprint size of the device. The use of smaller diameter couplant and vacuum lines also increases the flexibility of the supply lines and has the additional benefit of further reducing the forces that would cause flexible material 109 and 109' to break from the workpiece 101 resulting in the acoustic inspection device 1 to follow the orientation of workpiece 101 more accurately.

Still another feature of the present invention is the use of multi-piece flexible material 109 and 109', e.g., bristles. Thus those multiple pieces are individually free to locally flex in response to differences in the surface properties of workpiece 101 without disturbing other of the pieces of the flexible material. This greatly improves the ability of the present invention device to remain coupled to the workpiece. The prior art on the other hand employs a single piece mating surface which is prone to decouple from the workpiece.

It was observed during testing of the present invention that acoustic inspection device 1 was less influenced during use when multiple thinner, more flexible hoses, particularly for the vacuum hoses. When a single hose is used for the vacuum and couplant supply lines, hoes with a larger internal diameter are needed to provide the necessary volume. Such hoses are less flexible than the smaller hoses that are used when multiple hoses are used. Further, to prevent collapse, the vacuum hoses require thicker sidewalls the fewer vacuum hoses that are used, and that needed sidewall thickness was dramatically reduced as the number of vacuum hoses was increased since less vacuum needed to be drawn by each such hose. By reducing the sidewall thickness the hoses also become much more flexible. In fact it was discovered with as few as three or four vacuum hoses, the same hoses could be used for the vacuum lines as for the couplant lines where pressure and sidewall strength is much less critical. When only one hose is used for each of the vacuum and couplant supply lines, the vacuum hose is inherently less flexible than the couplant supply hose since thicker sidewalls are needed for the vacuum hose than for the couplant supply hose. The advantage of the more flexible and greater number of hoses had two observable advantages: 1) device 1 has an improved ability to remain coupled to the surface of the workpiece in any orientation; and there was a great reduction in the disturbance torque on device 1 presented by the hoses than when a single hose is used for the couplant and vacuum. The use of the single hoses favored one direction, whereas the uses of multiple hoses have a more uniformly distributed effect on device 1.

It was further observed that the use of multiple vacuum hoses resulted in an improvement in couplant recovery that requires less vacuum since the couplant recovery path length is reduced. An ancillary advantage obtained from the reduction in vacuum levels that are permit smaller vacuum hoses, is a savings in the necessary size and weight of support equipment of the scanning system.

Thus it can be seen that all of these features of the present invention contribute to the ability of acoustic inspection device 1 to follow, and remain coupled to, the surface of workpiece 101 regardless of the orientation of that surface, whether it be horizontal, angled or inverted.

Since the actual configuration of the acoustic inspection device of the present invention can be implemented in various configurations and is not limited to the example configuration discussed above, the scope of the present invention is only limited by the extend of the claims that follow.

What is claimed is:

1. An acoustical inspection device for inspecting a workpiece comprising:

a body defining a lower surface to be disposed opposite a workpiece and an inner passage through said body that is sized and shaped to receive an acoustic transducer;

an acoustically transparent membrane sealing an end of said inner passage at said lower surface of said body;

said body further defining therethrough a couplant supply passage with an inlet port position away from said lower surface disposed to receive couplant from an external source and an outlet port through said lower surface adjacent said end of said inner passage disposed to deliver couplant to said workpiece;

a first set of closely packed flexible material affixed to, and extending away from, said lower surface of said body surrounding and in spaced apart relationship with said end of said inner passage and said couplant outlet port;

said body further defining therethrough a vacuum chamber with an exhaust port positioned away from said lower surface disposed to expel recovered couplant to an external receptacle and an extraction port through said lower surface adjacent said flexible material on a side away from said end of said inner passage and said couplant outlet port; and a second set of closely packed flexible material affixed to, and extending away from, said lower surface of said body surrounding and in spaced apart relationship with said extraction port and said first set of closely packed flexible material.

* * * * *